United States Patent
Chen (12)

(10) Patent No.: US 6,339,714 B1
(45) Date of Patent: Jan. 15, 2002

(54) APPARATUS AND METHOD FOR MEASURING CONCENTRATIONS OF A DYE IN A LIVING ORGANISM

(76) Inventor: Bo Chen, 163 Dutch Rd., East Brunswick, NJ (US) 08816

( * ) Notice: Subject to any disclaimer, the term of this patent is extended or adjusted under 35 U.S.C. 154(b) by 0 days.

(21) Appl. No.: 09/394,913

(22) Filed: Sep. 13, 1999

(51) Int. Cl.[7] .................................................. A61B 5/00
(52) U.S. Cl. ........................ 600/314; 600/322; 600/324; 600/479
(58) Field of Search ................................ 600/310, 314, 600/322, 323, 324, 342, 431, 479, 481, 504, 526

(56) References Cited

U.S. PATENT DOCUMENTS

| | | |
|---|---|---|
| 3,677,648 A | 7/1972 | Dorsch |
| 4,281,645 A | 8/1981 | Jobsis |
| 4,972,331 A | 11/1990 | Chance |
| 5,154,176 A | 10/1992 | Kanda |
| 5,178,141 A * | 1/1993 | Kanda ........................ 600/322 |
| 5,251,632 A | 10/1993 | Delpy |
| 5,458,128 A | 10/1995 | Polanyl |
| 5,494,031 A | 2/1996 | Hoeft |
| 5,661,302 A | 8/1997 | Evans |
| 5,687,726 A | 11/1997 | Hoeft |
| 5,697,371 A | 12/1997 | Aoyagi |
| 5,706,808 A | 1/1998 | Kleinerman |
| 5,766,125 A * | 6/1998 | Aoyagi et al. ............... 600/310 |
| 5,865,757 A | 2/1999 | Hoeft |
| 5,999,841 A * | 12/1999 | Aoyagi et al. ............... 600/479 |

FOREIGN PATENT DOCUMENTS

| | | |
|---|---|---|
| EP | 0059032 | 2/1982 |
| WO | WO 95/03736 | 2/1995 |
| WO | WO 98/08434 | 3/1998 |

OTHER PUBLICATIONS

"Fick Principle" and "Indicator Dilution Techniques" Physiology, RM Berne & MN Levy, 2nd Edition, The C.V. Mosby Co. pp. 44–449.
"Blood Volume Measurement at the Bedide Using ICG Pulse Spectrophotometry" Haruna M. et al; Anesthesiology, 1998; 6:1322–1328.
"Cardiac Ouput and Circulation Blood Volume Analysis by Pulse Dye–Densitometry" Iijima T et al; J Clin Monit 1997; 13:81–89.
"Measurement of Cardiac Output by Pulse Dye Densitometry Using Indocyanine Green" Imai T; Anesthesiology, 1997; 87:816–822.
"Measurement of Cerebral Blood Flow in Newborn Infants Using Near Infrared Spectroscopy with Indocyanine Green" Patel J et al Pediatr Res 1998; 43:34–39.
"Measurement of Cerebral Blood Flow During Cardiopulmonary Bypass with Near–Infrared Spectroscopy" Roberts IG et al; J Thorac Cardiovasc Surg 1998; 115:94–102.
"Quantitation of Time– and Frequency–Resolved Optical Spectra for the Determnination of Tissue Oxygenation" Sevick EM et al; Analy Biochem 1991; 195:330–351.
"Pulse Oximetry" Yelderman M; Monitoring in Anestheisa and Critical Care Medicine 417–427.

* cited by examiner

Primary Examiner—Eric F. Winakur

(57) ABSTRACT

An apparatus and method for measuring indicator concentration time curves optically from a living organism using a single wavelength, by comparing the optical density before and after injection of the indicator and by selectively utilizing the values of the concentration of blood hemoglobin, blood oxygen saturation, or the mean optical pathlength in the computation. Whereby, physiological parameters such as cardiac output, blood flow and blood volume can be calculated by analyzing the indicator concentration time curves.

10 Claims, 2 Drawing Sheets

APPARATUS AND METHOD FOR MEASURING CONCENTRATIONS OF A DYE IN A LIVING ORGANISM

FIELD OF THE INVENTION

This invention relates to the measurement of dye concentrations in a living organism. More specifically, it relates to the optical measurement of the concentrations of an indicator dye in a living organism for the purpose of calculating physiological parameters such as cardiac output, blood flow and blood volume by analyzing the indicator concentration time curve (ICTC).

BACKGROUND OF THE INVENTION

Cardiac output (CO), blood flow (BF) and blood volume (BV), are important physiological parameters for evaluating the functions of vital organs. Therefore, measurements of these parameters are routinely performed in clinical practice as well as in research. Indicator dilution technique is a method commonly used to calculate CO, BF and BV. Generally, a known amount of indicator, such as a dye, or cold saline bolus, is introduced into the circulation via right atrium or central vein. Several ICTCs are then measured downstream in different parts of the body. CO can be calculated from the amount of the indicator and the ICTC from arterial blood. BF and BV of a vital organ can be calculated by analyzing the ICTCs simultaneously obtained from said vital organ and from the arterial blood.

Optical technology has been widely used to obtain ICTCs invasively and non-invasively for measuring CO, BF and BV. For example, U.S. Pat. Nos. 5,494,031 and 5,458,128 illustrate methods of calculating the concentrations of an indicator dye by utilizing the concentration of blood hemoglobin as a reference. However, these methods require light at least at two different wavelengths. Roberts I G, et al, (J Thorac Cardiovasc Surg 1998;1 15:94–102) has described a method of estimating cerebral blood flow and cerebral blood volume by simultaneously obtaining ICTCs of a dye (indocyanine green) from the arterial blood with a fiberoptic catheter and from the brain with a near infrared spectrometer. However, this method requires multiple wavelengths, which usually introduce a certain amount of error since the scattering of the light from the blood components and tissue are unequal at different wavelength.

SUMMARY OF THE INVENTION

An object of the present invention is to provide a new and improved apparatus and method for measuring ICTCs optically from the blood of a living organism using a single wavelength. Whereby, physiological parameters such as cardiac output, total blood volume and liver function can be calculated by analyzing the ICTCs.

It is another object of the present invention to provide a new and improved apparatus and method for measuring ICTCs optically from a vital organ using a single wavelength. Whereby, physiological parameters such as blood flow and blood volume of said vital organ could be calculated by analyzing the ICTCs simultaneously obtained both from the arterial blood and from said vital organ of the living organism. Further objects and advantages of the present invention will become apparent from a consideration of the drawings and ensuing description.

The foregoing objects and others are realized with the assumption that the blood oxygen saturation $SO_2$ and particularly the concentration of blood hemoglobin Hb of the living organism do not change during the brief measurement period. Prior studies indicated that this assumption is reasonable and changes in the optical attenuation after the dye injection is caused only by the absorption of the indicator dye (Kuebler W M, et al, J of Cerebral Blood Flow and Metabolism 1998:445–456). Furthermore, it is also assumed that the values of Hb and $SO_2$, which can be obtained using routine laboratory and oximetry methods, are available as references for calculating the concentrations of the indicator dye.

According to the present invention the methods of measuring ICTCs from the circulation, such as the arterial blood and from a vital organ, such as the brain of a living organism include: projecting light into the living organism; measuring optical density of the arterial blood $I(0)_a$ and optical density of the brain $I(0)_b$ at a single wavelength $\lambda$ before a predetermined initial time to establish the baseline values; introducing an indicator dye with known amount Q into the circulation via right atrium or central vein at the initial time; measuring optical density of the arterial blood $I(t)_a$ and optical density of the brain $I(t)_b$ after the initial time; measuring the concentration of blood hemoglobin Hb, blood oxygen saturation $SO_2$ and mean optical pathlength; computing the concentrations of the indicator dye in the arterial blood $C_d(t)_a$ and in the brain $C_d(t)_b$ by comparing $I(t)_a$ and $I(t)_b$ with their initial baseline values $I(0)_a$ and $I(0)_b$ and by selectively utilizing the values of the Hb, the $SO_2$ or the mean optical pathlength; and then obtaining the ICTCs by plotting $C_d(t)_a$ and $C_d(t)_b$ against time t.

In a practical application of the invention, the single wavelength $\lambda$ is chosen at around 800 nm. Indocyanine green (ICG), which has a maximum absorption at 800 nm, is used as the indicator dye. The optical density of the arterial blood can be obtained via a fiber optic catheter inserted into a radial artery, for example, or measured non-invasively using the arterial pulsatile signal similar to the method used by a pulse oximeter. Likewise, the optical density of the vital organs can be obtained via fiber optic probes attached to the cardiac muscle, for example, or measured from the brain non-invasively using a probe similar to the one used by a near infrared spectrometer.

DESCRIPTION OF THE PREFERRED EMBODIMENT

Figure 1:
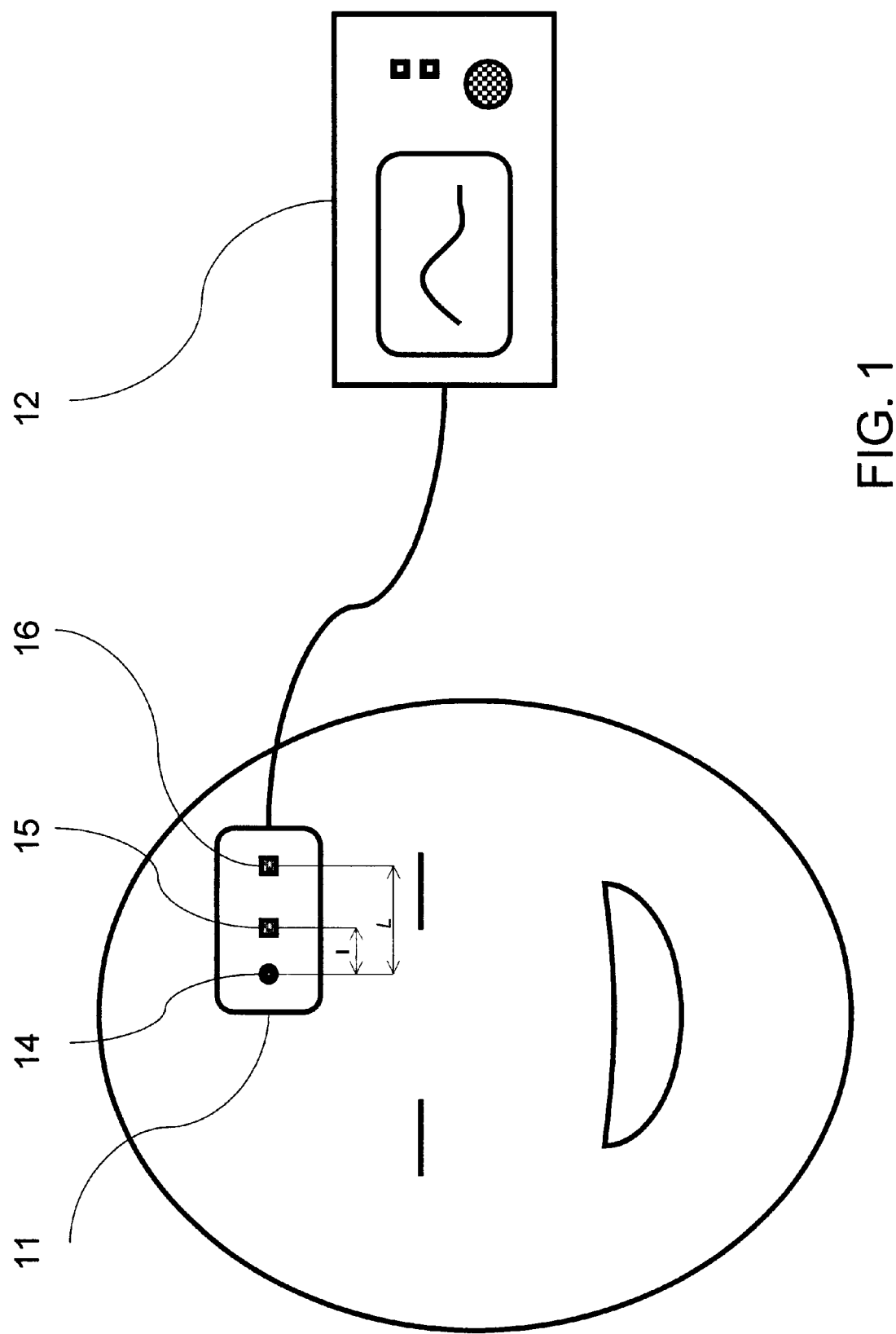
FIG. 1 is a schematic diagram showing a first embodiment of the present invention for the non-invasive measurement of ICTCs from the arterial blood and from the brain.

Referring now to the figures. FIG. 1 shows a schematic diagram of the first embodiment of the apparatus for non-invasive measurement of ICTCs from the arterial blood and from the brain of a human subject. This apparatus comprises an optical probe 11 that is connected to a controlling and computing unit 12. Said controlling and computing unit 12 is used to drive the light source, receive the detected signals, perform amplification, filtering, analog to digital conversion, calculate ICTCs and physiological parameters, and display or printout the results. The optical probe 11, which is applied to the forehead of a patient, comprises a light source 14, one near photodetector 15 and one far photodetector 16. The light source 14 can be a light emitting diode (LED) or a laser diode preferably having a wavelength at 800 nm. The distance l between the light source 14 and the near photodetector 15 is around 1.5~2.5 cm. Therefore, the near photodetector 15 is used mainly to detect the pulsatile signal from the arterial blood. The distance L between the light source 14 and the far photodetector 16 should be large (preferably>4 cm) so that the light will travel deep enough to reach the monitored brain tissue.

The signal detected by the near photodetector 15 is normalized using the method similar to the process in a pulse oximeter. The normalization process that is well known to those skilled in the art involves dividing the pulsatile component by the non-pulsatile component of the detected signal so as to obtain the attenuation $OD_a$ caused purely by the arterial blood Yelderman M, "Pulse Oximetry").

From the definition of arterial oxygen saturation $SaO_2$:

$$SaO_2 = \frac{C_{oa}}{C_{oa} + C_{ra}} \quad (1)$$

Wherein:

$C_{oa}$=concentration of arterial oxyhemoglobin (mmol/L of blood);

$C_{ra}$=concentration of arterial reduced hemoglobin (mmol/L of blood);

The concentration of blood hemoglobin Hb equal to the sum of the concentrations of oxyhemoglobin $C_{oa}$ and reduced hemoglobin $C_{ra}$ $$Hb = C_{oa} + C_{ra} \quad (2)$$

From equations (1) and (2):

$$C_{oa} = SaO_2 \cdot Hb \quad (3)$$

$$C_{ra} = (1 - SaO_2) \cdot Hb \quad (4)$$

From the near photodetector 15, before the injection of the indicator dye bolus at the initial time, the baseline attenuation of the arterial blood is given by:

$$OD(0)_a = (\epsilon_o C_{oa} + \epsilon_r C_{ra}) d \quad (5)$$

Wherein:

$\epsilon_o$=extinction coefficient of oxyhemoglobin at wavelength $\lambda$;

$\epsilon_r$=extinction coefficient of reduced hemoglobin at wavelength $\lambda$;

d=optical pathlength.

Indocyanine green (ICG), which has a maximum absorption at 800 nm, is used as the indicator dye. At the predetermined initial time, ICG with known amount Q is introduced into the circulation via central vein.

The essential idea of the present invention is the assumption that the arterial oxygen saturation $SaO_2$ and particularly the concentration of blood hemoglobin Hb are relative constant during the measurement period. Therefore changes in the optical attenuation after the ICG injection is caused only by the absorption of the ICG. By comparing the optical densities obtained before and after the injection of the ICG bolus, the influence of the absorption and scattering from hemoglobin and tissue can be eliminated. Accordingly, it is possible to calculate the absolute concentrations of the ICG in the arterial blood or in the brain tissue using only one wavelength.

Immediately after the injection of the ICG bolus at the initial time, the attenuation of the arterial blood is given by:

$$OD(t)_a = [\epsilon_o C_{oa} + \epsilon_r C_{ra} + \epsilon_d C_d(t)_a] d \quad (6)$$

Wherein:

$\epsilon_d$=extinction coefficient of said indicator dye at wavelength $\lambda$;

$C_d(t)_a$=concentration of arterial indicator dye at time t immediately after the initial time;

The time dependent ratio, R(t), of the attenuations OD(t)$_a$ OD(0)$_a$ is given by:

$$R(t) = \frac{OD(t)_a}{OD(0)_a} = \frac{\epsilon_o C_{oa} + \epsilon_r C_{ra} + \epsilon_d C_d(t)_a}{\epsilon_o C_{oa} + \epsilon_r C_{ra}} \quad (7)$$

From equations (3), (4) and (7), solve for the concentration of arterial indicator dye at time t:

$$C_d(t)_a = \frac{Hb}{\epsilon_d}[R(t) - 1] \cdot [(\epsilon_o - \epsilon_r)SaO_2 + \epsilon_r] \quad (8)$$

With the known values of Hb and $SaO_2$ measured by other means, equation (8) can be used to obtain the arterial ICTC by plotting $C_d(t)_a$ against time t. Whereby, many physiological parameters such as cardiac output, circulation and central blood volumes can be calculated by analyzing said arterial ICTC. The theories and methods of analyzing ICTCs have been well established. For example, with the known amount Q of the injected indicator dye, the cardiac output CO can be calculated using the well-known Stewart-Hamilton formula:

$$CO = \frac{Q}{\int C_d(t)_a dt} \quad (9)$$

Equation (8) can be further simplified if wavelength $\lambda$ is chosen at the isobestic point of the hemoglobin, 800 nm, where $\epsilon_o = \epsilon_r$, therefore:

$$C_d(t)_a = \frac{\epsilon_r}{\epsilon_d} Hb[R(t) - 1] \quad (10)$$

According to equation (10), measurement of $SaO_2$ becomes unnecessary. This has particular advantages not only because Hb is generally more constant than $SaO_2$, but also because changes of $SaO_2$ will not affect the measurement of ICTCs.

From the far photodetector 16, before the injection of the ICG bolus at the initial time, the baseline attenuation $OD(0)_b$ of the brain is given by a modified Beer-Lambert equation, which describes optical attenuation in a highly scattering medium:

$$OD(0)_b = \ln\frac{I_{ob}}{I(0)_b} = (\epsilon_o C_{ob} + \epsilon_r C_{rb})BL + G \quad (11)$$

Wherein:

$I_{ob}$=incident light intensity to the brain;

$I(0)_b$=detected baseline light intensity from the brain;

$C_{ob}$=concentration of cerebral oxyhemoglobin (mmol/L of brain tissue);

$C_{rb}$=concentration of cerebral reduced hemoglobin (mmol/L of brain tissue);

B=differential pathlength factor;

L=distance between the light source the photodetector;

G=attenuation due to scattering & geometry;

Immediately after the injection of the ICG bolus at the initial time, the attenuation $OD(t)_b$ of the brain at time t is given by:

$$OD(t)_b = \ln\frac{I_{ob}}{I(t)_b} = [\varepsilon_o C_{ob} + \varepsilon_r C_{rb} + \varepsilon_d C_d(t)_b]BL + G \quad (12)$$

Wherein:

$C_d(t)_b$ concentration of cerebral indicator dye at time t;
From equations (11) and (12), solve for the concentration of cerebral indicator dye at time t:

$$C_d(t)_b = \frac{1}{\varepsilon_d BL}\ln\frac{I(0)_b}{I(t)_b} \quad (13)$$

With the known values of B and L, equation (13) can be used to obtain the brain ICTC by plotting $C_d(t)_a$ against time t. Using both the cerebral ICTC and a simultaneously measured arterial ICTC from equation (8) or (10), cerebral blood flow and cerebral blood volume can be determined.

In a highly scattering medium such as tissue, the photons travel a mean distance that is far greater than the distance between the light source and the photodetector. In equation (13), the differential pathlength factor B is the scaling factor for defining the true optical distance—the differential pathlength DP=BL. The differential pathlength factor B is unitless and approximately constant for a given tissue. For example, B is average about 6 for adult heads and 5 for neonate heads at the wavelength 807 nm. Numerous studies have shown that it is feasible to use a constant B value for a given tissue to calculate concentrations of a light absorbing material. However, small amount of individual variations of B exists. There are methods and instruments that are able to calculate on-line the differential pathlength DP. These include the time of flight method and intensity modulation method (Sevick E M et al; Analy Biochem 1991; 195:330–351) that can be readily incorporated in the present apparatus for more accurate calculation of concentrations of the indicator dye. These methods of estimating the differential pathlength are well known to those skilled in the art. The one that would be chosen in a practical implementation of the present invention should be based on the accuracy requirement of the measurement and the price performance ratio. After all, the essential concept of the present invention will not be affected regardless what method is chosen for estimating the mean optical pathlength of photons travel through said living organism.

Obviously, said optical probe 11 can have only one near photodetector to measure the arterial ICTC for calculating cardiac output and circulating blood volume. In that case, said single detector probe is preferably applied to nose, finger, or ear lobe so that the pulsatile signal from the arterial blood can be easily captured. Furthermore, for certain applications such as monitoring from a neonate head a single detector probe is adequate for obtaining both the pulsatile signals from the arterial blood and the optical density of the brain tissue. Yet another option is to have more photodetectors that have different separation distances from the light source so that the detected signal would reflect the response of the brain tissue at different depth.

Figure 2:
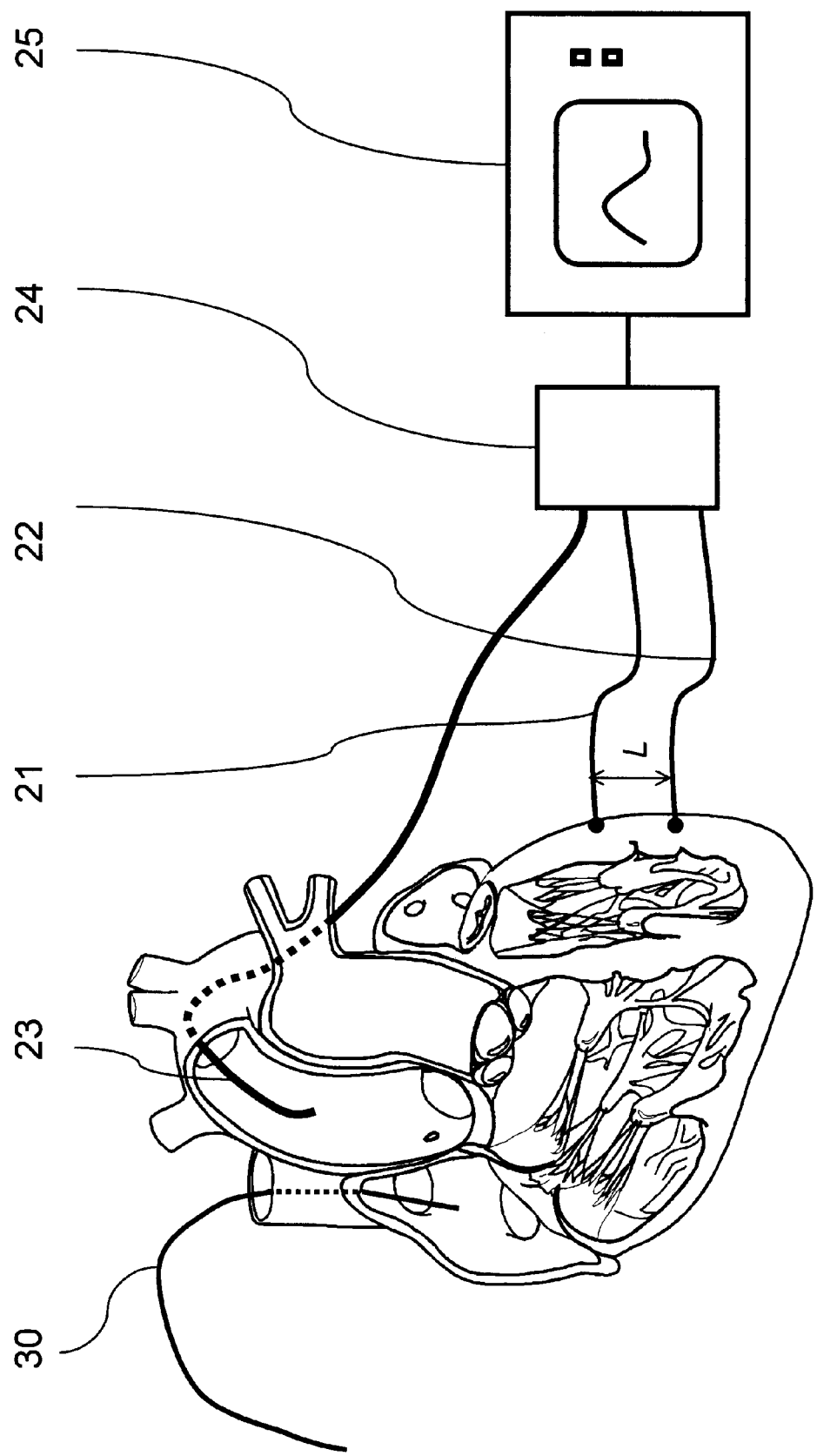
FIG. 2 is a schematic diagram of a second embodiment of the invention for the measurement of ICTCs from the arterial blood and from the cardiac muscle directly.

FIG. 2 shows the second embodiment of the method and apparatus of the present invention for simultaneously obtaining ICTCs from the arterial blood and the cardiac muscle, for example, in a research laboratory setting. The apparatus comprises a catheter 23, a light delivery probe 21 and a light receiving probe 22, all connected to an interface 24 that is linked to a controlling and computing unit 25. Both the catheter and the probes use fiber optics to transmit light at a single wavelength λ, preferably at 800 nm. Said controlling and computing unit 25 is used to drive the light source, receive the detected signals, perform amplification, filtering, analog to digital conversion, calculate ICTCs and physiological parameters, and display or printout the results.

Said catheter 23 is inserted into the aorta via a femoral or a brachial artery of the subject to measure the optical density in the arterial blood directly. The method of the second embodiment comprising steps similar to the first embodiment of the present invention that include: measuring baseline optical densities from the arterial blood via catheter 23 and from the cardiac muscle via fiber optic probes 22 before a predetermined initial time; measuring the concentration of blood hemoglobin Hb and the arterial oxygen saturation $SaO_2$; introducing a known amount Q of ICG into the circulation via a catheter 30 at the initial time; measuring optical densities from the arterial blood and from the cardiac muscle immediately after the initial time; obtaining the arterial ICTC using equation (8) or (10) and the ICTC of the cardiac muscle using an equation similar to equation (13).

$$C_d(t)_c = \frac{1}{\varepsilon_d BL}\ln\frac{I(0)_c}{I(t)_c} \quad (14)$$

Wherein:

$I(0)_c$=detected baseline light intensity from the cardiac muscle;

$I(t)_c$=detected light intensity from the cardiac muscle at time t immediately after the initial time;

$C_d(t)_c$=concentration of indicator dye of the cardiac muscle at time t immediately after the initial time;

Whereby physiological parameter such as cardiac output, blood flow and blood volume of the cardiac muscle can be calculated by analyzing the ICTCs from the arterial blood and from the cardiac muscle.

It is obvious that one can combine said catheter 23 in FIG. 2 with a head probe similar to the optical probe 11 in FIG. 1, probably with only a single far photodetector, to obtain the arterial ICTC and the cerebral ICTC. This is particularly useful for the situations where the arterial pulsatile signals are weak or absent, for instance, during a cardiac surgery when the patient is on a heart-lung machine. As a result, parameters such as cardiac output and cerebral blood flow can be measured during this critical period when the brain is likely to sustain ischemic insults. Likewise, one can also obtain the arterial ICTC non-invasively to avoid arterial catheterization, while simultaneously using fiber optic probes to measure the ICTC directly from the cardiac muscle.

Obviously, the single wavelength catheter 23 can be used separately to measure the arterial ICTC from an artery of a living organism directly for calculating parameters like CO. In addition, the application of the single wavelength catheter 23 is not only limited to the measurement of ICTCs from the arterial blood. For example, the catheter 23 can be inserted into a vein to measure venous ICTCs using equation (8) or (10). Whereby, liver function can be evaluated from the ICG clearance calculated form the venous ICTCs. Clearly, if equation (8) is used to obtain venous ICTCs, the arterial oxygen saturation $SaO_2$ in equation (8) should be replaced by the venous oxygen saturation measured from the venous blood.

I claim:

1. A method of measuring concentrations of a light-absorbing material in a living organism, comprising the steps of:

a) directing light into the living organism at a chosen site;
b) detecting light transmitted through or reflected from the living organism at one wavelength and determining its optical intensity at a time before a predetermined initial time;
c) measuring the concentration of blood hemoglobin;
d) injecting a defined amount of said light-absorbing material absorbing light at said wavelength into the circulatory system of the living organism at said initial time;
e) detecting light transmitted through or reflected from the living organism at said wavelength and determining its optical intensity immediately after said initial time;
f) calculating concentrations of said light-absorbing material by comparing the optical intensities of said one wavelength detected before and after said initial time and by utilizing the value of said concentration of blood hemoglobin;
g) determining the concentration time curve of said light-absorbing material;
h) to determine physiological parameters analyzing said concentration time curve.

2. The method of claim 1, further comprising measuring blood oxygen saturation, and then calculation concentrations of said light-absorbing material by comparing the optical intensities detected before and after said initial time and by utilizing the values of said concentration of blood hemoglobin and said blood oxygen saturation.

3. The method of claim 1 or 2, wherein using the pulsatile components of the light intensities are used to compute a normalized signal that is generated only from the arterial blood of said living organism, and the concentration time curve of said light-absorbing material in the arterial blood of said living organism is determined non-invasively.

4. A method of measuring concentrations of a light-absorbing material in a living organism, comprising the steps of:
a) directing light into the living organism at a chosen site;
b) detecting light transmitted through or reflected from the living organism at one wavelength and determining its optical intensity at a time before a predetermined initial time;
c) injecting a defined amount of said light-absorbing material absorbing light at said wavelength into the circulatory system of the living organism at said initial time;
d) detecting light transmitted through or reflected from the living organism at said wavelength and determining its optical intensity immediately after said initial time;
e) estimating the mean optical pathlength of photons traveling through said living organism;
f) calculating concentrations of said light-absorbing material by comparing the optical intensities of said one wavelength detected before and after said initial time and by utilizing the value of said mean optical pathlength;
g) determining the concentration time curve of said light-absorbing material;
h) to determine physiological parameters analyzing said concentration time curve.

5. The method of claim 1, 2 or 4, wherein light is directed and detected non-invasively at a chosen site of said living organism.

6. The method of claim 1, 2 or 4, wherein light is directed and detected via optical means inserted into a chosen site of said living organism.

7. The method of claim 1, 2 or 4, wherein measurements are performed at least at two sites of said living organism simultaneously, and said physiological parameters are calculated by analyzing said concentration time curves from said at least two.

8. The method of claim 4, wherein said mean optical pathlength of photons traveling through said living organism is estimated utilizing the distance L between the light directing and detecting means and a constant B predetermined for a specific tissue of said living organism.

9. The method of claim 4, wherein said mean optical pathlength of photons traveling through said living organism is estimated on-line by measuring the time of flight of an optical pulse through said living organism.

10. The method of claim 4, wherein said mean optical pathlength of photons traveling through said living organism is estimated on-line by measuring the phase shift of the intensity modulated light through said living organism.

* * * * *